United States Patent
Ohtawa et al.

(10) Patent No.: US 8,138,136 B2
(45) Date of Patent: Mar. 20, 2012

(54) PROCESS FOR PRODUCTION OF ALKYLENE OXIDE ADDUCTS

(75) Inventors: Yasuki Ohtawa, Wakayama (JP);
Toshihiro Tanaka, Wakayama (JP);
Kaoru Ohmae, Wakayama (JP)

(73) Assignee: Kao Corporation, Tokyo (JP)

( * ) Notice: Subject to any disclaimer, the term of this patent is extended or adjusted under 35 U.S.C. 154(b) by 310 days.

(21) Appl. No.: 12/514,465

(22) PCT Filed: Oct. 29, 2007

(86) PCT No.: PCT/JP2007/071032
§ 371 (c)(1),
(2), (4) Date: May 12, 2009

(87) PCT Pub. No.: WO2008/059709
PCT Pub. Date: May 22, 2008

(65) Prior Publication Data
US 2010/0056821 A1    Mar. 4, 2010

(30) Foreign Application Priority Data
Nov. 13, 2006  (JP) ................................. 2006-306926

(51) Int. Cl.
*C11D 1/22*  (2006.01)
(52) U.S. Cl. .................... 510/421; 510/342; 510/360
(58) Field of Classification Search .................. None
See application file for complete search history.

(56) References Cited

U.S. PATENT DOCUMENTS

| 3,539,519 | A | * | 11/1970 | Weimer ......................... 568/625 |
| 4,340,766 | A | * | 7/1982 | Klahr et al. ................... 568/625 |
| 5,057,628 | A | | 10/1991 | Edwards et al. |
| 7,402,644 | B2 | * | 7/2008 | Inaoka et al. ................. 526/320 |

FOREIGN PATENT DOCUMENTS

| CN | 1649813 A | | 8/2005 |
| JP | 53119809 | * | 10/1978 |
| JP | 1 199928 | | 8/1989 |
| JP | 2001-096153 | | 4/2001 |
| JP | 2002 326969 | | 11/2002 |
| JP | 2003 277309 | | 10/2003 |

OTHER PUBLICATIONS

U.S. Appl. No. 12/993,859, filed Nov. 22, 2010, Ohtawa, et al.
Office Action issued on Aug. 3, 2011 in the corresponding Chinese Patent Application No. 200780041980.8 (with English Translation).
Office Action issued Nov. 22, 2011 in Japanese Patent Application No. 2006-306926 (w/English translation).

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for producing an alkyleneoxide adduct, including the steps of reacting an aliphatic alcohol containing a hydrocarbon group having 6 to 22 carbon atoms with an alkyleneoxide in the presence of a catalyst to obtain a reaction product containing an alkyleneoxide adduct; and subjecting the reaction product successively to acid treatment and reduction treatment, and an alkyleneoxide adduct having a carbonyl value of 5 μmol/g or less. The alkyleneoxide adduct is useful as a raw material of various anionic surfactants, and the anionic surfactants derived from the alkyleneoxide adduct are free from undesirable coloration.

19 Claims, No Drawings

PROCESS FOR PRODUCTION OF ALKYLENE OXIDE ADDUCTS

FIELD OF THE INVENTION

The present invention relates to a process for producing high-quality alkyleneoxide adducts, and also relates to the alkyleneoxide adducts.

BACKGROUND OF THE INVENTION

In recent years, nonionic surfactants in the form of an alkyleneoxide-low mole adduct of aliphatic alcohols, etc., which have a narrow molecular weight distribution have been noticed. If techniques for efficiently producing the low mole adducts are established, there is such an advantage that various anionic surfactants are derived from these low mole adducts as nonionic surfactants by further subjecting the nonionic surfactants to sulfonation reaction, phosphorization reaction, etc.

Hitherto, basic catalysts such as KOH have been extensively used for producing alkyleneoxide adducts. However, when using such basic catalysts, there tends to occur such a problem that the resulting nonionic surfactants have a broad molecular weight distribution. In 1970s, acid catalysts such as boron trifluoride and indium chloride have been noticed, whereas in 1980s to 1990s, homogeneous catalysts such as metal alcoholates, or heterogeneous catalysts such as phosphates of rare earth metals and mixed metal oxides have been noticed. However, it is known that even if it is attempted to produce the low mole adducts, for example, using a heterogeneous catalyst such as lanthanum phosphate catalyst, the resulting nonionic surfactants fail to have a narrow molecular weight distribution.

For example, Non-Patent Document 1 discloses that when using the heterogeneous catalysts, it is possible to obtain ethyleneoxide-7 mole adducts having a narrow molecular weight distribution, but the obtained ethyleneoxide-1 mole or 2 mole adducts are only those having a broad molecular weight distribution similarly to the case where the basic catalysts such as KOH are used. In addition, Non-Patent Document 2 discloses that even when using the heterogeneous catalysts such as mixed metal oxides composed of magnesium oxide and aluminum, it is difficult to obtain ethyleneoxide-1 mole adducts having a narrow molecular weight distribution.

On the other hand, Patent Documents 1 to 3 disclose nonionic surfactants composed of alkyleneoxide adducts of aliphatic alcohols. In addition, Patent Document 4 discloses a catalyst for alkoxylation of an aliphatic alcohol and an alkyleneoxide, and an alkyleneoxide adduct produced by using the catalyst. However, when these alkyleneoxide adducts are subjected to anionization process such as sulfation to derive anionic surfactants therefrom, there tends to occur such a problem that the resulting anionic surfactants suffer from undesirable coloration.

Non-Patent Document 1: "Nonionic Surfactants Organic Chemistry", volume 72, p. 32
Non-Patent Document 2: "Oleo-Science", Vol. 2, p. 97 (2002)
Patent Document 1: JP 53-119809A
Patent Document 2: JP 2001-11489A
Patent Document 3: JP 2001-40391A
Patent Document 4: JP 2005-305280A

SUMMARY OF THE INVENTION

The present invention relates to (1) a process for producing an alkyleneoxide adduct, including the steps of reacting an aliphatic alcohol containing a hydrocarbon group having 6 to 22 carbon atoms with an alkyleneoxide in the presence of a catalyst to obtain a reaction product containing an alkyleneoxide adduct; and subjecting the reaction product successively to acid treatment and reduction treatment, and (2) an alkyleneoxide adduct produced by the above process which has a carbonyl value of 5 μmol/g or less.

DETAILED DESCRIPTION OF THE INVENTION

The present invention relates to a process for producing an alkyleneoxide adduct that is useful as a raw material of various anionic surfactants and capable of producing such an anionic surfactant as a derivative thereof which is free from undesirable coloration, and the alkyleneoxide adduct.

The present inventors have found that when subjecting a reaction product containing an alkyleneoxide adduct of aliphatic alcohol successively to acid treatment and reduction treatment, the above conventional problems can be solved.

Thus, the present invention relates to the following aspects (1) and (2):

(1) A process for producing an alkyleneoxide adduct, including the steps of reacting an aliphatic alcohol containing a hydrocarbon group having 6 to 22 carbon atoms with an alkyleneoxide in the presence of a catalyst to obtain a reaction product containing an alkyleneoxide adduct; and subjecting the reaction product successively to acid treatment and reduction treatment.

(2) An alkyleneoxide adduct produced by the process as defined in the above aspect (1) which has a carbonyl value of 5 μmol/g or less.

The aliphatic alcohol containing a hydrocarbon group having 6 to 22 carbon atoms used in the present invention is not particularly limited, and is an aliphatic alcohol containing a linear or branched, saturated or unsaturated hydrocarbon group having preferably 6 to 22 carbon atoms and more preferably 8 to 20 carbon atoms.

Examples of the suitable aliphatic alcohol include saturated chain-like aliphatic alcohols such as various hexyl alcohols, various octyl alcohols, various decyl alcohols, various dodecyl alcohols, various tetradecyl alcohols, various cetyl alcohols, various heptadecyl alcohols, various octadecyl alcohols, various nonadecyl alcohols and various arachyl alcohols; unsaturated chain-like aliphatic alcohols such as various hexenyl alcohols, various octenyl alcohols, various decenyl alcohols, various dodecenyl alcohols, various tridecenyl alcohols, various pentadecenyl alcohols and various octadecenyl alcohols; cyclic aliphatic alcohols such as methylcyclohexyl alcohol, ethylcyclohexyl alcohol, n-propylcyclohexy alcohol, octylcyclohexyl alcohol, nonylcyclohexyl alcohol and adamantyl alcohol; and aromatic group-containing aliphatic alcohols such as benzyl alcohol and cinnamyl alcohol. Among these aliphatic alcohols, from the viewpoints of good reactivity and utilizability, preferred are saturated aliphatic alcohols, and more preferred is at least one compound selected from the group consisting of octyl alcohols, dodecyl alcohols, tridecyl alcohols, tetradecyl alcohols, hexadecyl alcohols and octadecyl alcohols.

These aliphatic alcohols may be used singly or in the form of a mixture of any two or more thereof.

The alkyleneoxide used in the present invention is not particularly limited, and is preferably an alkyleneoxide containing an alkanediyl group having 2 to 4 carbon atoms and preferably 2 or 3 carbon atoms. Specific examples of the alkyleneoxide include ethyleneoxide, trimethyleneoxide, propane-1,2-diyl oxide and tetramethyleneoxide. Among these alkyleneoxides, preferred is at least one compound selected from the group consisting of ethyleneoxide, trimethyleneoxide and propane-1,2-diyl oxide, and more preferred is ethyleneoxide.

These alkyleneoxides may be used singly or in the form of a mixture of any two or more thereof.

The catalyst used in the present invention is not particularly limited, and is preferably an acid catalyst and more preferably a water-soluble and water-stable acid catalyst. The water-soluble and water-stable acid catalyst is easily recovered and reused. The term "water-soluble and water-stable" catalyst as used herein means that the catalyst has a solubility in 100 g of water of 1 g or more as measured at the temperature used upon recovery of the catalyst, and is free from hydrolysis even when reacted with water.

The acid catalyst is preferably a Lewis acid, more specifically, a compound represented by the following general formula (2):

$$M[R^2SO_3]_m \qquad (2).$$

In the general formula (2), M represents at least one element selected from the group consisting of copper (Cu), zinc (Zn), cadmium (Cd), molybdenum (Mo), iron (Fe) and rare earth elements; m is an integer equivalent to a valence of the element M; and $R^2$ is a perfluoroalkyl group having 1 to 16 carbon atoms.

Among the rare earth elements, preferred are scandium (Sc), yttrium (Y) and lanthanoids. Of the lanthanoids, preferred is lanthanum (La). Among the above metals M, preferred are copper (Cu), zinc (Zn), yttrium (Y) and lanthanum (La), and more preferred is lanthanum (La).

$R^2$ is a perfluoroalkyl group preferably having 1 to 10 carbon atoms and more preferably 1 to 5 carbon atoms.

The atomic group $[R^2SO_3]$ represents a perfluoroalkylsulfonic group. Specific examples of the perfluoroalkylsulfonic group include a trifluoromethanesulfonic group, a pentafluoroethanesulfonic group, a heptafluoropropanesulfonic group, a nonafluorobutanesulfonic group, an undecafluoropentanesulfonic group, a tridecafluorohexanesulfonic group, a pentadecafluoroheptanesulfonic group and a heptadecafluorooctanesulfonic group. Among these perfluoroalkylsulfonic groups, preferred are a trifluoromethanesulfonic group, a pentafluoroethanesulfonic group, a heptafluoropropanesulfonic group and a nonafluorobutanesulfonic group, and more preferred are a trifluoromethanesulfonic group and a pentafluoroethanesulfonic group.

From the above viewpoints, especially suitable acid catalysts are those catalysts containing a perfluoroalkyl group having 1 to 5 carbon atoms such as lanthanum trifluoromethanesulfonate, lanthanum pentafluoroethanesulfonate, yttrium trifluoromethanesulfonate, yttrium pentafluoroethanesulfonate, copper (II) trifluoromethanesulfonate, copper (II) pentafluoroethanesulfonate, zinc trifluoromethanesulfonate and zinc pentafluoroethanesulfonate. Among these acid catalysts, preferred are lanthanum trifluoromethanesulfonate, yttrium trifluoromethanesulfonate, copper (II) trifluoromethanesulfonate and zinc trifluoromethanesulfonate, and more preferred is lanthanum trifluoromethanesulfonate.

The acid catalyst composed of the compound represented by the above general formula (2) may be produced by known methods. For example, the compound of the general formula (2) may be synthesized by the methods described in T. Mukaiyama, N. Iwasawa, R. W. Stevens and T. Haga, "Tetrahedron", 40, 1381 (1984) and JP 2005-305280A.

Examples of the acid catalysts other than the compound represented by the above general formula (2) include a mixture of an acid and a metal alkoxide, and metal halides such as antimony pentachloride, boron trifluoride and indium chloride.

The acid used in the mixture of an acid and a metal alkoxide is preferably sulfuric acid, the metal used therein is preferably aluminum, and the alkoxide used therein is preferably an alkoxide containing an alkyl group having 1 to 8 carbon atoms and more preferably 2 to 4 carbon atoms. The mixture of an acid and a metal alkoxide is especially preferably a mixture of sulfuric acid and aluminum isopropoxide. The mixing ratio of the acid to the metal alkoxide in the mixture is preferably from 0.1 to 5.0 and more preferably from 0.5 to 2.0.

These acid catalysts may be used singly or in the form of a mixture of any two or more thereof.

The amount of the acid catalyst used in the present invention is preferably from 0.001 to 5 mol %, more preferably from 0.005 to 3 mol % and still more preferably from 0.01 to 2 mol % on the basis of the aliphatic alcohol containing a hydrocarbon group having 6 to 22 carbon atoms from the viewpoints of a high reaction rate and a good economy.

The proportions of the aliphatic alcohol and the alkyleneoxide are not particularly limited, and may be controlled from a good utilizability, etc., such that the molar ratio of the alkyleneoxide to the aliphatic alcohol (alkyleneoxide/aliphatic alcohol) is preferably from 0.5 to 2.5, more preferably from 0.5 to 2.0 and still more preferably from 0.8 to 1.8.

In the present invention, the alkyleneoxide addition reaction may be conducted under a solvent-free condition or in a solvent. When the addition reaction is conducted in the solvent, an inert organic solvent such as cyclohexane and toluene may be used in an amount of usually from 10 to 30% by mass. From the industrial viewpoints, it is preferred that the addition reaction be conducted under a solvent-free condition.

The alkyleneoxide addition reaction is preferably conducted at a temperature of from 60 to 160° C., more preferably from 60 to 140° C. and still more preferably from 60 to 120° C. from the viewpoints of a high reaction rate and a high quality of the obtained product. The reaction pressure is preferably from 0.005 to 0.7 MPa and more preferably from 0.01 to 0.5 MPa from the viewpoint of a high reaction rate.

In the present invention, the catalyst removal step may be conducted. For example, the reaction product may be subjected to adsorption treatment using an adsorbent such as "KYOWAAD 600" (tradename) available from Kyowa Chemical Industry Co., Ltd., and then to filtration procedure to remove the catalyst therefrom. In this case, if required, the filtration procedure may be conducted using a diatomaceous earth-based filtration assistant (such as, for example, "RADIOLITE" available from Showa Chemical Industry Co., Ltd.) to shorten the time required for the filtration.

The thus obtained alkyleneoxide adduct is a compound represented by the following general formula (1):

$$R^1O(AO)_nH \qquad (1)$$

wherein $R^1$ is a hydrocarbon group having 6 to 22 carbon atoms; AO is an alkanediyloxy group having 2 to 4 carbon atoms; and n represents an average number of addition of AO groups and is a number of from 0.1 to 5.

In the above general formula (1), $R^1$ is preferably a linear or branched, saturated or unsaturated hydrocarbon group having 8 to 20 carbon atoms.

Examples of the suitable hydrocarbon group include saturated chain-like hydrocarbon groups such as various hexyl groups, various octyl groups, various decyl groups, various dodecyl groups, various tetradecyl groups, various cetyl groups, various heptadecyl groups, various octadecyl groups, various nonadecyl groups and various arachyl groups; unsaturated chain-like hydrocarbon groups such as various hexenyl groups, various octenyl groups, various decenyl groups, various dodecenyl groups, various tridecenyl groups, various pentadecenyl groups and various octadecenyl groups; alicyclic hydrocarbon groups such as methylcyclohexyl group, ethylcyclohexyl group, n-propylcyclohexyl group, octylcyclohexyl group, nonylcyclohexyl group and adamantyl group; and aromatic hydrocarbon groups such as benzyl group and cinnamyl group. Among these hydrocarbon groups, from the viewpoints of a good reactivity and a good utilizability, preferred are saturated chain-like hydrocarbon groups, and more preferred are octyl groups, dodecyl groups, tridecyl groups, tetradecyl groups, hexadecyl groups and octadecyl groups.

Specific examples of the alkanediyloxy group having 2 to 4 carbon atoms as AO in the general formula (1) include ethyleneoxy group, trimethyleneoxy group, propane-1,2-diyloxy group and tetramethyleneoxy group. Among these alkanediyloxy groups, preferred is at least one group selected from the group consisting of ethyleneoxy group, trimethyleneoxy group and propane-1,2-diyloxy group, and more preferred is ethyleneoxy group.

The average molar number n of addition of AO is preferably from 0.1 to 3 and more preferably from 0.1 to 2.

When n lies within the above specified range, derivatives obtained from the above alkyleneoxide adduct advantageously exhibit a high performance. Meanwhile, the (AO) groups in number of n may be composed of the same one kind of group or different two or more kinds of groups. When different two or more kinds of AO groups are present, the $(AO)_n$ may be in the form of either a random addition or a block addition. The order of addition of the groups is not particularly limited.

In the present invention, the thus obtained reaction product containing the alkyleneoxide adduct is successively subjected to acid treatment and then to reduction treatment.

The reason why the alkyleneoxide adduct (nonionic surfactant) and various anionic surfactants derived therefrom are undesirably colored when using the acid catalyst, is not clearly determined. However, it is not considered that the undesirable coloration is caused only by an aliphatic aldehyde as a by-product which is an oxide of the aliphatic alcohol used as the raw material, etc. That is, it is considered that the undesirable coloration of various anionic surfactants is caused mainly by the presence of an acetal as a by-product which is produced by reacting the aliphatic aldehyde and/or an aldehyde produced from the alkyleneoxide such as ethyleneoxide with the aliphatic alcohol as the raw material or the obtained alkyleneoxide adduct.

For this reason, before conducting the sulfation reaction, etc., the reaction product containing the alkyleneoxide adduct is subjected to acid treatment to remove the acetal, etc., therefrom, and then to reduction treatment to remove the aldehyde compounds therefrom. By conducting such treatments, it has been found that when various anionic surfactants are derived from the nonionic surfactant through the sulfation step, etc., the aimed compounds can be produced without any undesirable coloration.

The "acid treatment" as used herein means that the reaction product containing the alkyleneoxide adduct is contacted with an acid substance under an acid condition preferably having a pH of 3 or less and more preferably a pH of from 1 to 2. Specific examples of the acid substance include inorganic acids such as hydrochloric acid, sulfuric acid, nitric acid and phosphoric acid; and organic acids such as succinic acid and oxalic acid.

The temperature used upon contacting the reaction product containing the alkyleneoxide adduct with the acid substance is not particularly limited as long as the acetal can be hydrolyzed, and is preferably from 30 to 150° C., more preferably from 50 to 100° C. and still more preferably from 70 to 90° C. The time of contact between the reaction product and the acid substance is also not particularly limited as long as the acetal can be hydrolyzed, and is preferably from 1 to 24 h and more preferably from 2 to 10 h.

Meanwhile, it is preferred that before conducting the reduction treatment, the reaction product be subjected to neutralization treatment using an alkali substance such as sodium hydroxide, potassium hydroxide and sodium carbonate.

The "reduction treatment" as used herein means that the reaction product is reduced using a reducing agent such as sodium borohydride and lithium aluminum hydride.

The reduction reaction temperature is not particularly limited as long as the aldehyde compound can be reduced, and is preferably from 0 to 100° C., more preferably from 20 to 90° C. and still more preferably from 40 to 80° C. The reduction reaction time is also not particularly limited as long as the aldehyde compound can be reduced, and is preferably from 0.5 to 24 h, more preferably from 1 to 10 h and still more preferably from 2 to 5 h.

The amount of the acetal by-produced may be measured by determining a carbonyl value (COV) of the reaction product. When the carbonyl value is increased, the color of the obtained product tends to be deteriorated. When successively subjecting the reaction product to the acid treatment and then to the reduction treatment according to the present invention, the carbonyl value of the resulting alkyleneoxide adduct can be adjusted to preferably 5 µmol/g or less, more preferably 3 µmol/g or less, still more preferably 2 µmol/g or less and further still more preferably 1.5 µmol/g or less. Meanwhile, the carbonyl value may be measured according to ASTM E411.

The alkyleneoxide adduct of aliphatic alcohol having a carbonyl value of 2 µmol/g or less, in particular, 1.5 µmol/g or less, can be produced under the suitable conditions used in the process of the present invention.

Also, the alkyleneoxide adduct produced by the process of the present invention has a high quality without any undesirable coloration, and exhibits a color (APHA) of preferably from 1 to 30 and more preferably from 1 to 20 as measured according to JIS K-0071-1. Thus, the alkyleneoxide adduct of the present invention can be used as such or may be further subjected to anionization such as sulfation to derive various anionic surfactants therefrom. The thus obtained alkyleneoxide adduct and anionic surfactants may be suitably used in extensive applications as components of shampoos, dish detergents, metal detergents, emulsifiers for polymerization and other chemical products.

EXAMPLES

Example 1

An autoclave equipped with a stirrer, a temperature controller and an automatic feeder was charged with 186 g (1.0 mol) of dodecyl alcohol and 7.6 g (0.013 mol) of lanthanum trifluoromethanesulfonate as a catalyst, and an inside of the mixture system was purged and replaced with nitrogen. Thereafter, the contents in the autoclave were dehydrated under reduced pressure (1.3 kPa) at 110° C. for 0.5 h. Next, while introducing 66 g (1.5 mol) of ethyleneoxide (EO) into the autoclave such that the reaction system was kept under a pressure of from 0.1 to 0.4 MPa at 80° C., the reaction was conducted. After introducing the ethyleneoxide, the reaction was conducted at 80° C. for 3 h.

After completion of the ethyleneoxide addition reaction, unreacted ethyleneoxide was removed under reduced pressure, thereby obtaining a reaction product. As a result of analyzing the reaction product by a gas chromatography, it was confirmed that the purity of one mole adduct contained in the obtained alkoxylate was 44%. It was also confirmed that the carbonyl value (COV) of the reaction product was 5.3 μmol/g.

Next, the thus obtained reaction product was transferred into a four-necked glass flask, and then 0.4 g of sulfuric acid and 10% of water based on the reaction product were added thereto. After confirming that the pH of the resulting mixture was 2 or less, the mixture was subjected to acid treatment at 80° C. for 3 h. Then, after the reaction mixture was mixed with a sodium hydroxide aqueous solution to render the mixture alkaline, 0.025 g of sodium borohydride was added thereto, and the obtained mixture was subjected to reduction treatment at 80° C. for 2 h. The thus obtained reduction treatment product had a carbonyl value of 1.0 μmol/g. The results are shown in Table 1.

Example 2

The same procedure as in Example 1 was repeated except for using a mixture (0.004 mol) of sulfuric acid (0.6 g) and aluminum isopropoxide (0.9 g) in place of lanthanum trifluoromethanesulfonate, and introducing 44 g (1.0 mol) of ethyleneoxide (EO) into the reaction system. The results are shown in Table 1.

Example 3

The same procedure as in Example 2 was repeated except for using 1.2 g (0.004 mol) of antimony pentachloride in place of the mixture of sulfuric acid and aluminum isopropoxide. The results are shown in Table 1.

Example 4

The same procedure as in Example 2 was repeated except for using 214 g (1.0 mol) of tetradecyl alcohol in place of dodecyl alcohol. The results are shown in Table 1.

Comparative Example 1

The same procedure as in Example 1 was repeated except for subjecting the reaction product to no acid treatment (no addition of sulfuric acid and water; no treatment at 80° C. for 3 h). The results are shown in Table 1.

TABLE 1-1

| | Alcohol | | Alkyleneoxide | | Catalyst | |
|---|---|---|---|---|---|---|
| | Kind | Mol | Kind | Mol | Kind | Mol |
| Example 1 | Dodecyl alcohol | 1.0 | EO | 1.5 | Lanthanum trifluoromethanesulfonate | 0.013 |
| Example 2 | Dodecyl alcohol | 1.0 | EO | 1.0 | Mixture of sulfuric acid and aluminum isopropoxide | 0.004 |
| Example 3 | Dodecyl alcohol | 1.0 | EO | 1.0 | Antimony pentachloride | 0.004 |
| Example 4 | Tetradecyl alcohol | 1.0 | EO | 1.0 | Mixture of sulfuric acid and aluminum isopropoxide | 0.004 |
| Comparative Example 1 | Dodecyl alcohol | 1.0 | EO | 1.5 | Lanthanum trifluoromethanesulfonate | 0.013 |

TABLE 1-2

| | Purity* (%) | COV** before treatment | Acid treatment | Reduction treatment | COV** after treatment | Color*** (APHA) |
|---|---|---|---|---|---|---|
| Example 1 | 44 | 5.3 | Done | Done | 1.0 | 5 |
| Example 2 | 48 | 16 | Done | Done | 0.9 | 5 |
| Example 3 | 48 | 2.1 | Done | Done | 1.1 | 10 |
| Example 4 | 48 | 18 | Done | Done | 1.1 | 5 |
| Comparative Example 1 | 44 | 5.3 | None | Done | 5.9 | 5 |

Note

*Purity of one mole adduct

**Unit of carbonyl value (COV): μmol/g

***Color (APHA) was measured according to JIS K-0071-1

INDUSTRIAL APPLICABILITY

According to the production process of the present invention, the obtained alkyleneoxide adduct is capable of producing the aimed compounds without any undesirable coloration when various anionic surfactants are derived therefrom through sulfation step, etc.

The invention claimed is:

1. A process for producing an alkyleneoxide adduct, comprising:
   reacting an aliphatic alcohol with an alkyleneoxide in the presence of a catalyst, thereby obtaining a reaction product comprising the alkyleneoxide adduct;
   acid treating the reaction product, and
   reducing the acid treated reaction product,
   wherein the aliphatic alcohol comprises a hydrocarbon group having 6 to 22 carbon atoms, and
   wherein the alkyleneoxide adduct is a compound represented by the formula (1):

$$R^1O(AO)_nH \qquad (1),$$

wherein
   $R^1$ is a hydrocarbon group having 6 to 22 carbon atoms;
   AO is an alkanediyloxy group having 2 to 4 carbon atoms; and
   n is a number from 0.1 to 5.

2. The process according to claim 1, wherein the acid treatment comprises contacting the reaction product with an acid substance under an acid condition having a pH of 3 or less.

3. The process according to claim 1, wherein the catalyst is an acid catalyst.

4. An alkyleneoxide adduct produced by the process as defined in claim 1, wherein the alkyleneoxide adduct has a carbonyl value of 5 μmol/g or less.

5. The process for producing an alkyleneoxide adduct according to claim 3, wherein the acid catalyst is a Lewis acid.

6. The process for producing an alkyleneoxide adduct according to claim 5, wherein the Lewis acid is represented by formula (2):

$$M[R^2SO_3]_m \qquad (2)$$

wherein
   M represents at least one element selected from the group consisting of copper(Cu), zinc (Zn), cadmium (Cd), molybdenum (Mo), iron (Fe) and a rare earth element,
   m is an integer equivalent to a valence of the element M; and
   $R^2$ is a perfluoroalkyl group having 1 to 16 carbon atoms.

7. The process according to claim 6, wherein the Lewis acid represented by formula (2) is selected from the group consisting of lanthanum trifluoromethanesulfonate, lanthanum pentafluoroethanesulfonate, yttrium trifluoromethanesulfonate, yttrium pentafluoroethanesulfonate, copper (II) trifluoromethanesulfonate, copper (II) pentafluoroethanesulfonate, zinc trifluoromethanesulfonate and zinc pentafluoroethanesulfonate.

8. The process for producing an alkyleneoxide adduct according to claim 3, wherein the acid catalyst is a mixture of an acid and a metal alkoxide.

9. The process for producing an alkyleneoxide adduct according to claim 2, wherein the acid substance contacted with the reaction product is an inorganic or organic acid.

10. The process for producing an alkyleneoxide adduct according to claim 9, wherein the inorganic acid is selected from the group of acids consisting of hydrochloric acid, sulfuric acid, nitric acid and phosphoric acid.

11. The process for producing an alkyleneoxide adduct according to claim 9, wherein the organic acid is succinic acid or oxalic acid.

12. The process according to claim 1, further comprising neutralizing the acid treated reaction product before reducing.

13. The process according to claim 1, wherein the reducing the acid treated reaction product comprises reacting with a reducing agent.

14. The process according to claim 13, wherein the reducing agent is sodium borohydride or lithium aluminum hydride.

15. The process according to claim 12, wherein the reducing the neutralized acid treated reaction product comprises reacting with a reducing agent.

16. The process according to claim 15, wherein the reducing agent is sodium borohydride or lithium aluminum hydride.

17. The process according to claim 1, further comprising removing the catalyst before the acid treatment of the reaction product.

18. The process according to claim 17, wherein removing the catalyst comprises adsorbing onto an adsorbent and filtering the adsorbent treated reaction product to remove the catalyst.

19. The process according to claim 1, wherein a carbonyl value of the alkyleneoxide adduct of the reduced acid treated reaction product is 5 μmol/g or less.

* * * * *